United States Patent [19]
Kreikebaum et al.

[11] Patent Number: 5,600,438
[45] Date of Patent: *Feb. 4, 1997

[54] PARTICLE SENSOR WITH VARIABLE-SPEED BLOWER

[75] Inventors: Gerhard Kreikebaum, San Bernandino; David L. Chandler, Highland, both of Calif.

[73] Assignee: Venturedyne, Ltd., Milwaukee, Wis.

[ * ] Notice: The term of this patent shall not extend beyond the expiration date of Pat. No. 5,515,164.

[21] Appl. No.: 616,456

[22] Filed: Mar. 15, 1996

Related U.S. Application Data

[63] Continuation of Ser. No. 364,389, Dec. 23, 1994, Pat. No. 5,515,164, which is a continuation of Ser. No. 109,007, Aug. 19, 1993, abandoned.

[51] Int. Cl.⁶ .......................... G01N 21/05; G01N 21/53
[52] U.S. Cl. ..................... 356/339; 356/246; 250/576
[58] Field of Search .................. 356/335–343, 356/244, 246, 436, 440, 441, 442; 250/574, 576, 564, 222.2; 377/10, 11, 53

[56] References Cited

U.S. PATENT DOCUMENTS

| | | | |
|---|---|---|---|
| 2,535,181 | 12/1950 | Way | 88/14 |
| 3,248,551 | 4/1966 | Frommer | 250/218 |
| 3,678,847 | 7/1972 | Ludewig, Jr. et al. | 340/236 |
| 3,739,180 | 6/1973 | Carlson | 356/335 |
| 3,840,304 | 10/1974 | Hirafugi | 356/201 |
| 3,984,786 | 10/1976 | Pike | 331/94.5 L |
| 4,132,894 | 1/1979 | Yule | 250/435 |
| 4,273,443 | 6/1981 | Hogg | 356/343 |
| 4,571,079 | 2/1986 | Knollenberg | 356/336 |
| 4,746,215 | 5/1988 | Gross | 356/339 |
| 4,842,406 | 6/1989 | VonBargen | 356/336 |
| 4,984,889 | 1/1991 | Sommer | 356/336 |
| 5,011,286 | 4/1991 | Petralli | 356/343 |
| 5,033,851 | 7/1991 | Sommer | 356/338 |
| 5,084,629 | 1/1992 | Petralli | 250/573 |
| 5,351,855 | 10/1994 | Nelson et al. | 236/44 C |

OTHER PUBLICATIONS

E G & G Rotron Custom Division, Woodstock, NY; "Low Voltage (4.8–12VDC) Electronically Communtated D.C. Model R203 ECDC"—#1001, Jan., 1991.

*Primary Examiner*—Hoa Q. Pham
*Attorney, Agent, or Firm*—Jansson & Shupe, Ltd.

[57] ABSTRACT

Disclosed is a particle sensor having a light beam with a beam long axis and an air flow tube with an inlet end and a particle exit mouth. In an aspect of the invention, the cross-sectional area of the flow passage at the inlet end is greater than the cross-sectional area of the exit mouth. This enlarged area dramatically reduces pressure drop along the tube. The exit mouth is in registry with the light beam and is elongate in a direction substantially parallel to the beam long axis. Thus, particles flowing through the mouth pass through the beam. In another aspect, the invention includes a centrifugal blower which is light in weight and which may be battery powered.

4 Claims, 8 Drawing Sheets

PARTICLE SENSOR WITH VARIABLE-SPEED BLOWER

RELATED APPLICATION

This application is a continuation of application Ser. No. 08/364,389 filed on Dec. 23, 1994, now U.S. Pat. No. 5,515,164 which, in turn, is a continuation of application Ser. No. 08/109,007 filed on Aug. 19, 1993, and now abandoned.

FIELD OF THE INVENTION

This invention relates generally to air quality and, more particularly, to instruments for assaying airborne particulates.

BACKGROUND OF THE INVENTION

Particle counters and sensors are used to detect light scattered by particles entrained in a stream of fluid, e.g., in an air stream. Such counters and sensors draw air (with entrained particles) from a room, for example, and flow such air along a tube and through an illuminated sensor "view volume" to obtain information about the number and size of such particles. Such information results from an analysis of the very small amounts of light reflectively "scattered" by the particle as it moves through the view volume.

Some types of sensors flow such air along an enclosed transparent tube; others "project" the air and accompanying particles at a particular flow rate (often measured in cubic feet per minute) from one tube across an open space to another tube. In sensors of the latter type, there is no tube wall (however transparent such wall may be) to impair light scattering and collecting. In other words, the particle is briefly illuminated by a very-small-diameter light beam is it "flies" through an open space.

Among other uses, particle counters incorporating particle sensors are used to obtain a measure of air quality by providing information as to the number and size of particles present in some specified volume of air, e.g., a cubic meter of air. Even work environments which appear to human observation to be clean—business offices, manufacturing facilities and the like—are likely to have substantial numbers of microscopic airborne particles. While such particles are not usually troublesome to the human occupants, they can create substantial problems in certain types of manufacturing operations.

For example, semiconductors and integrated chips are made in what are known as "clean rooms," the air in which is very well filtered. In fact, clean rooms are usually very slightly pressurized using extremely clean air so that particle-bearing air from the surrounding environs does not seep in. And the trend in the semiconductor and integrated chip manufacturing industry is toward progressively smaller products.

A small foreign particle which migrates into such a product during manufacture can cause premature failure or outright product rejection even before it is shipped to a customer. This continuing "miniaturization" requires corresponding improvements in clean-room environments (and in the related measuring instruments) to help assure that the number and size of airborne particles are reduced below previously-acceptable levels. While known particle counters and sensors have been generally acceptable for their intended purpose, certain disadvantages exist.

A disadvantage of known particle sensors involves the air passage, usually circular, along which air and entrained particles flow. In particular, such passage has a very small cross-sectional area. As a result, the pressure differential between the ends of the passage (sometimes referred to as the "pressure drop" across the passage) is quite high. It is not unusual to encounter a pressure drop in the range of 25–70 inches of water at a flow rate of about one cubic foot per minute (CFM). In the field of particle sensors, a pressure drop of 25–70 inches of water at that air flow rate is typical.

(Parenthetically, measuring pressure in inches of water is common. An analogy is found in older style blood pressure measuring devices which include a column of mercury contained in and visible through a graduated glass tube. Blood pressure is measured in "millimeters of mercury" and in such older style devices, blood pressure was equal to the column height. Blood pressure is still measured in millimeters of mercury but a different type of gauge is used to make the measurement.)

Because of the typical pressure drop along the very-small-area air flow passage, known sensors require a motor-driven positive displacement vacuum pump, usually of the diaphragm or vane type, to create enough vacuum to overcome such pressure drop. The necessary electric drive motor and vacuum pump are likely to be relatively heavy. And the motor requires outlet-sourced power; battery power is not practical because of the relatively large amount of power consumed. And because such a sensor requires an electrical cord and plug, it is not so readily moved from site to site, especially remote sites.

While the pressure drop along the air flow passage can be reduced by increasing the passage cross-sectional area, there is another design constraint which militates against that approach. To help assure accuracy in particle sensing and counting, all (or substantially all) of the air-entrained particles flowing along the passage must pass through the beam of light. Usually, the "flight path" of particles is perpendicular to such beam. However, the light beam is preferably sharply focused and its diameter is very small, e.g., less than about 0.1 inch. Therefore, the diameter of the air flow passage cannot be appreciably larger than that of the light beam and still assure that most or all of the particles will pass through the light beam and be detected.

The invention addresses these seemingly intractable difficulties and inconsistent design parameters in a unique and imaginative way.

OBJECTS OF THE INVENTION

It is an object of the invention to provide an improved particle sensor overcoming some of the problems and shortcomings of the prior art.

Another object of the invention is to provide an improved particle sensor in which the air flow passage exhibits exceptionally low pressure drop at a flow rate of about one CFM.

Another object of the invention is to provide an improved particle sensor in which substantially all of the particles are directed through the light beam.

Yet another object of the invention is to provide an improved particle sensor which is lighter in weight than comparable conventional sensors.

Still another object of the invention is to provide an improved particle sensor which is battery powered and highly portable, even to remote sites. How these and other objects are accomplished will become more apparent from the following descriptions and from the drawing.

SUMMARY OF THE INVENTION

The invention is an improvement in a particle sensor of the type having a light beam with a beam long axis and also having an air flow tube with (a) an inlet end, and (b) a particle exit mouth. In the improvement, the cross-sectional area of the flow passage at the inlet end is quite large and is greater than the cross-sectional area of the exit mouth. And the exit mouth is elongate in a direction substantially parallel to the beam long axis and, preferably, is "race-track" shaped and has first and second side edges which are generally parallel to one another.

The flow passage (of relatively large area) dramatically reduces the pressure drop along the tube. And the long, relatively narrow exit mouth (about as wide as the width of the light beam) helps assure that particles flowing through the mouth pass through the beam.

More specifically, the air flow tube has an inlet portion and a nozzle portion. The latter has a first inlet section which has a minimum cross-sectional area, i.e., an area less than that of any section along the length of the inlet portion. Further, the nozzle portion has a first nozzle section which has a maximum cross-sectional area, i.e., an area greater than that of any section along the nozzle portion.

In a highly preferred embodiment, the cross-sectional area of the first inlet section is no less than the cross-sectional area of the first nozzle section. Additionally, the inlet portion has an enlarged second inlet section having a cross-sectional area greater than that of the first inlet section. The first inlet section and the first nozzle section have substantially the same shape, e.g., circular.

In another aspect of the invention, the sensor air flow tube extends along a flow axis and the sensor has an air blower (preferably a centrifugal blower) rather than the conventional positive-displacement vacuum pump. The blower has an inlet opening which is substantially circular and in concentric registry with the flow axis. In fact, the new sensor has several component parts "stacked" along the flow axis so that particle flow from the inlet portion to the blower is in a straight line.

In another aspect, the new sensor makes unique use of a small centrifugal blower. Such blowers are used in applications other than particle sensors and are employed for their output flow rather than for their ability to "pull a vacuum." In the invention, it is the blower air entry port, not the flow-emanating exhaust port which is of interest. The air entry port is in flow communication with the exit mouth and the blower thereby provides the pressure differential between the inlet end and the exit mouth of the air flow tube.

In fact, substantially all of the air passing through the blower (preferably a centrifugal blower) is drawn from and first through the air flow tube. In that way, the sensor is substantially unaffected by blower-generated contaminants.

The sensor has a sensing cavity and a blower cavity separated from the sensing cavity by a wall. The wall has an aperture through it and the blower is mounted to an annular plate having an opening through it. The aperture and the opening are also in registry with the flow axis.

In yet other aspects of the invention, the air blower is battery powered. While battery-powered air blowers per se are known, earlier designers in the field of particle sensors have never appreciated how to construct an air flow path with sufficiently low pressure drop along its length that a very low power blower could be used and still provide very good air flow rate. A preferred blower is of the adjustable speed type for selecting an air flow rate. Speed adjustment may include closed loop control in connection with a flow meter.

Other detail of the invention are set forth in the following detailed description and in the drawing.

DETAILED DESCRIPTION OF PREFERRED EMBODIMENTS

Referring first to FIGS. 1 through 5, the improved sensor 10 includes a sensing portion 11 with a sensor block 13 and a light-scatter sensing cavity 15. The cavity 15 has a reflecting mirror 17, e.g., an elliptical mirror, and a detector 19 mounted to receive scattered light 24 scattered by a particle 23 and reflected by the mirror 17. Referring also to FIGS. 6–11, an air flow tube 25 is mounted to the block 13, extends along a flow axis 27 and includes a slightly tapered inlet end 29 for attaching one end of a length of hose 31. A probe (not shown) is attached to the other end of the hose 31 and air with entrained particles flows through the hose 31 and the flow tube 25 and is expelled at the exit mouth 33.

Figure 1:
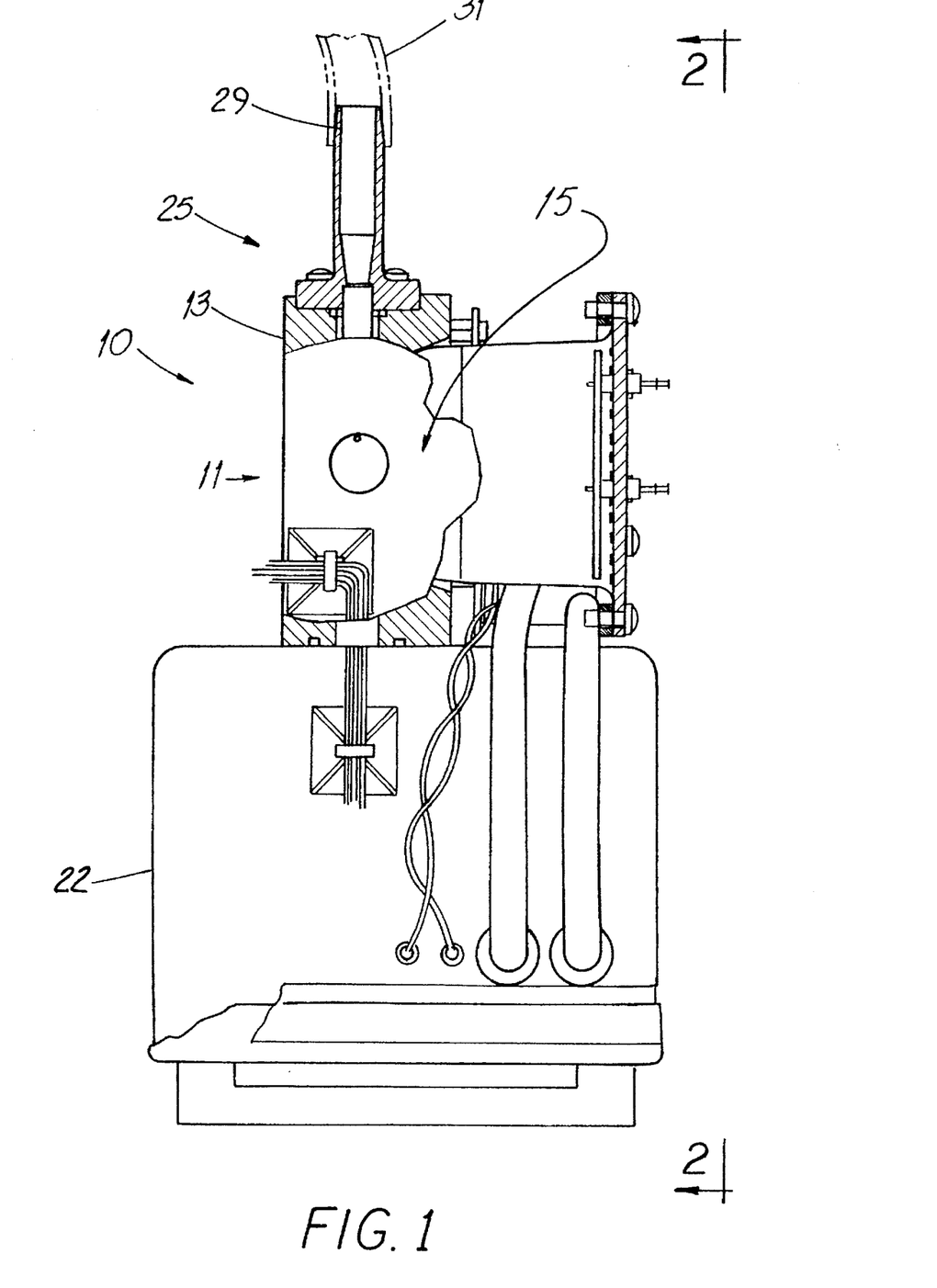
FIG. 1 is a side elevation view of the new sensor. Parts are broken away and other parts are shown in cross-section.

The sensing portion 11 also includes a laser diode assembly 35 which provides a very thin, substantially cylindrical beam of light 21 along a beam axid 37. The axis 39, the beam long axis 37 and the flow axis 27 are preferably orthogonal; that is, they are mutually perpendicular.

Figure 2:
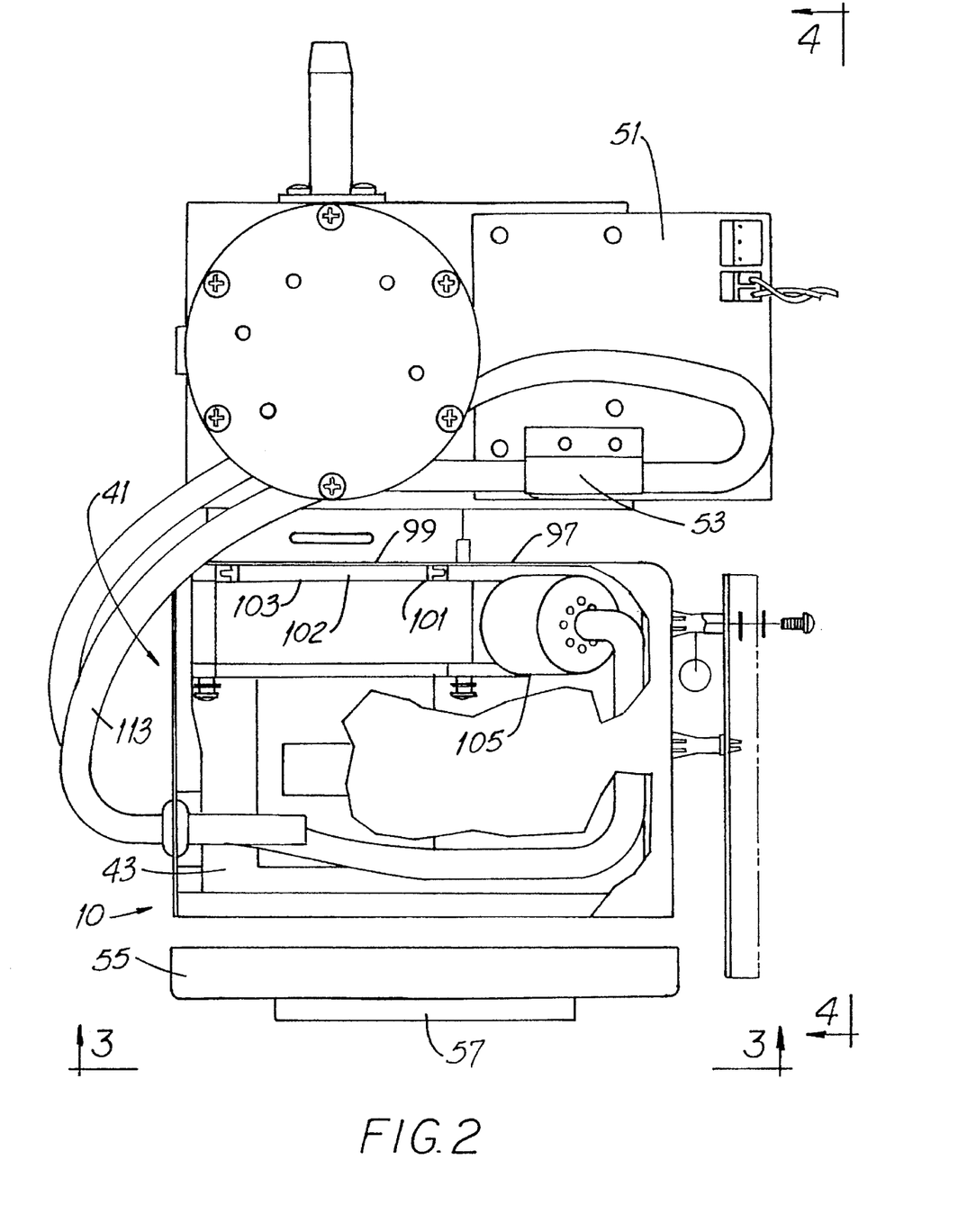
FIG. 2 is an elevation view of the new sensor taken along the viewing plane 2—2 of FIG. 1. The upper and lower portions and the cover of the sensor are slightly spaced from one another and parts are broken away.
Figure 3:
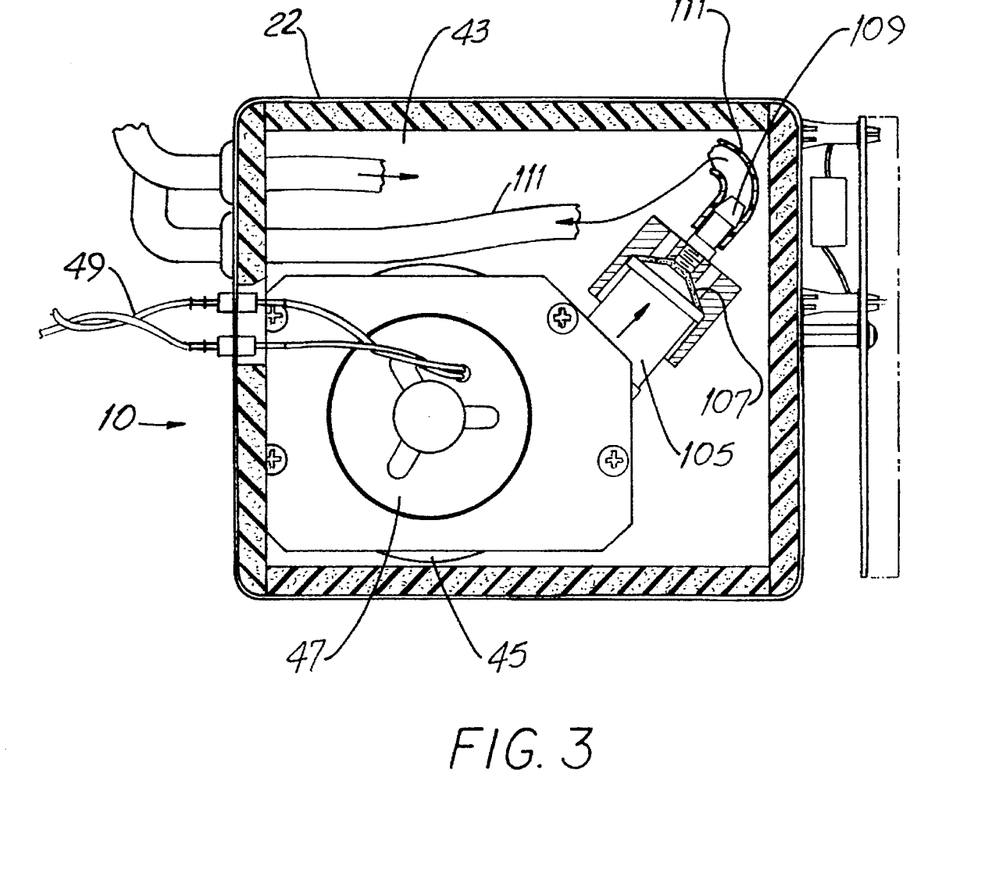
FIG. 3 is a bottom view of the sensor taken along the viewing plane 3—3 of FIG. 2. Parts are broken away, other parts are shown in cross-section and yet other parts are omitted.
Figure 4:
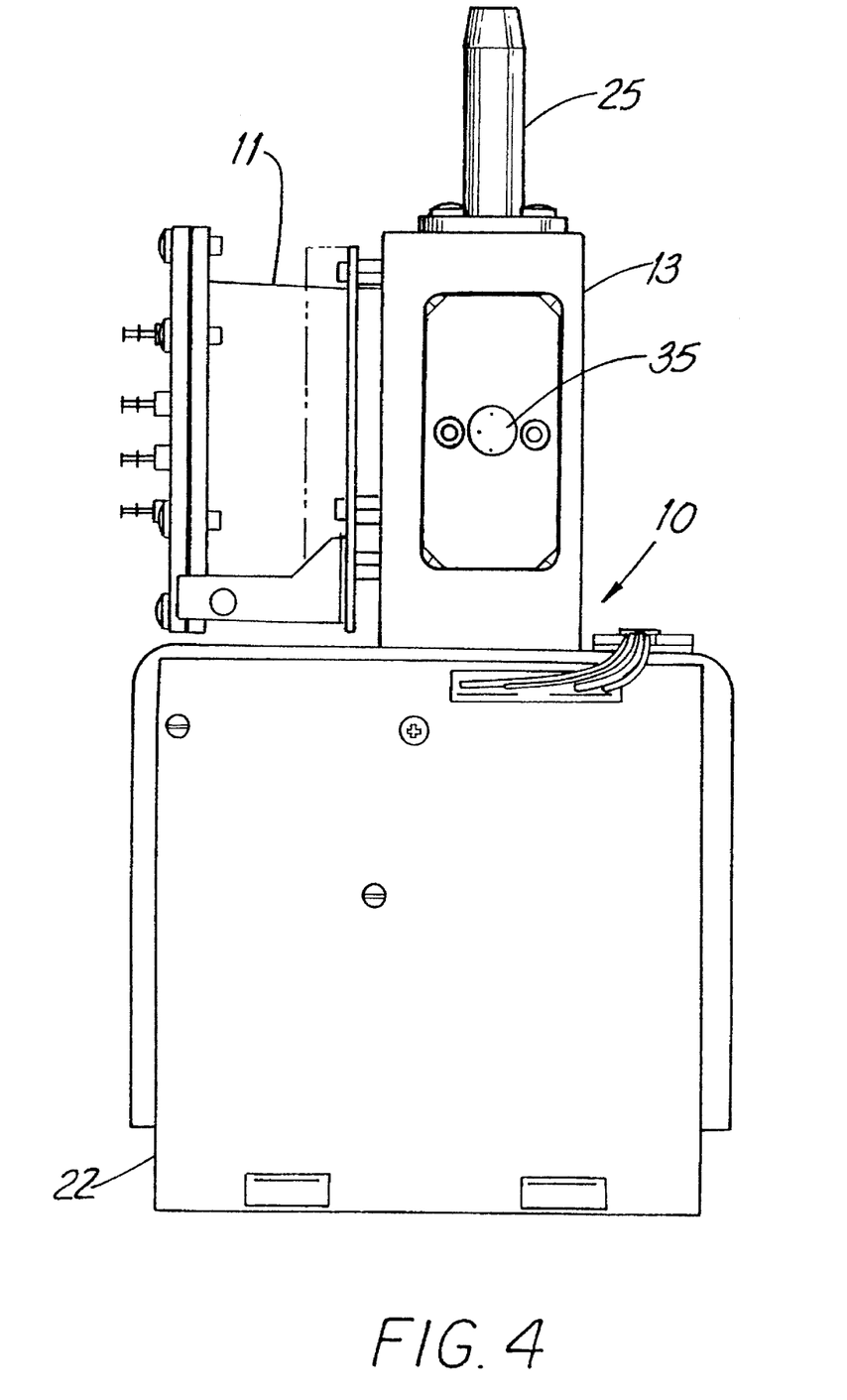
FIG. 4 is an elevation view of the sensor taken along the viewing plane 4—4 of FIG. 2. The parts shown as slightly spaced in FIG. 2 are fully assembled in FIG. 4.

As best seen in FIGS. 2 and 3, the sensor 10 also has a housing 22 with a blower portion 41 including a blower cavity 43 in which is mounted an air blower 45 with an electric drive motor 47 attached thereto. Such motor may be AC or DC, the latter for easier battery-powered portability. Battery power is provided to the motor 47 through the leads 49. A printed circuit board 51 provides closed loop feedback control for speed regulation at a set point selected using the flow sensor 53. Speed control is by pulse width modulation.

The bottom cover 55 of the cavity 43 has an exhaust filter 57 through which must pass all air flowing through the sensor 10. The filter 57 helps avoid contaminating the environment (which may be a "clean room") with particulates sloughed from the blower 45 itself and/or drawn in through the air flow tube 25.

Before describing particular details of a preferred air flow tube 25, an overview comment will be helpful. In general, the air flow tube 25 has a relatively large cross-sectional area 58 at its inlet end 29. Viewed from left to right in FIG. 11, such cross-sectional area 58 remains substantially constant along a first segment 59 of the tube 25 and then gradually diminishes at a second segment 61. Its smallest cross-sectional area is at the exit mouth 33. The following more detailed description is based upon that general configuration.

Referring particularly now to FIGS. 6–11, the air flow tube 25 includes an inlet portion 63 (which is generally T-shaped in cross-section) and a nozzle portion 65, the upstream end 67 of which is snugly fitted into a pocket 69 formed in the downstream end 71 of the portion 63. Particularly, the upstream end 67 abuts an annular shoulder 73, the inward edge 75 of which defines an area 76 having substantially the same size and shape as the area 76 defined by the inner surface 77 of the upstream end 67. Preferably, those areas 76 are circular and of substantially the same diameter.

Figure 11:
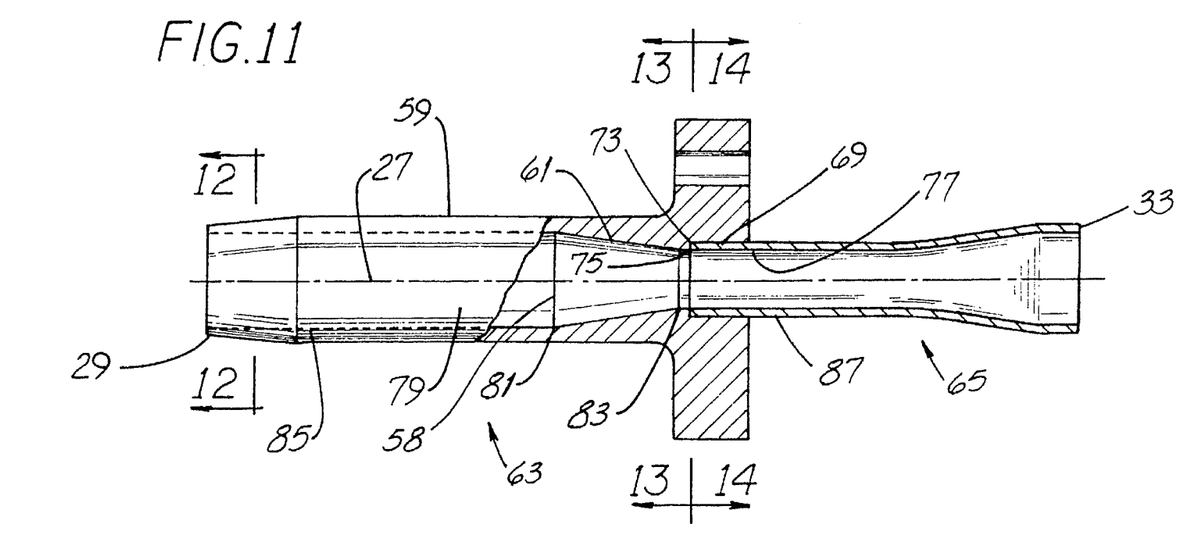
FIG. 11 is a side elevation view in cross-section of the inlet portion of FIGS. 6 and 7 and the nozzle portion of FIGS. 8–10 assembled to one another.
Figure 12:
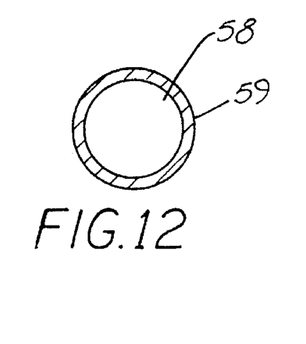
FIG. 12 is a cross-section view of the inlet portion of the air flow tube taken along the viewing plane 12—12 of FIG. 11.
Figure 13:
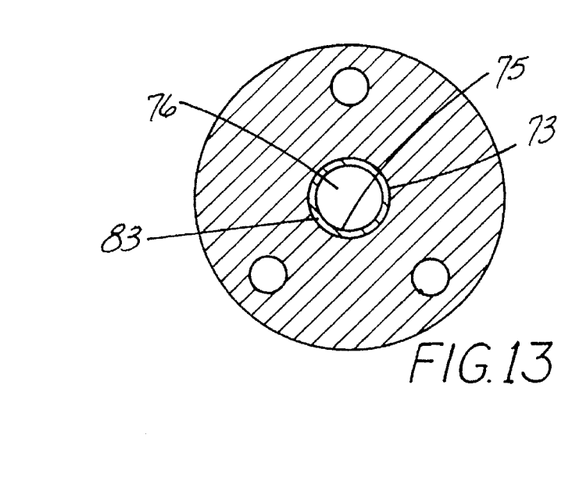
FIG. 13 is a cross-section view of the inlet portion of the air flow tube taken along the viewing plane 13—13 of FIG. 11.
Figure 14:
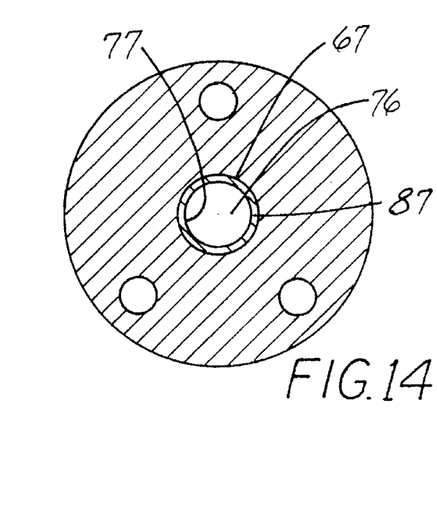
FIG. 14 is a cross-section view of the nozzle portion of the air flow tube taken along the viewing plane 14—14 of FIG. 11.

The area of the passage 79 in the inlet portion 63 gradually increases from the shoulder 73 leftward as viewed in FIG. 11. The passage 79 attains maximum area 58 at a location 81 between the inlet end 29 and the segment 61. In a highly preferred arrangement, the segment 61 resembles a truncated cone.

Certain features of the preferred air flow tube 25 will now be described using a few "sections," i.e. profiles like cross-sectional views as aspects of the tube 25 would appear if cut through by an intersecting plane. Referring now to FIGS. 11–14, the inlet portion 63 has a first inlet section 83 of minimum cross-sectional area 76. That is, the cross-sectional area 76 of the inlet section 83 is less than the comparable area at any other section along the length of the inlet portion 63. And the inlet portion 63 has a second inlet section 85 having a cross-sectional area 58 greater than that of the first inlet section 83. This relationship is apparent from a comparison of FIGS. 12 and 13.

The nozzle portion 65 has a first nozzle section 87 of maximum cross-sectional area. The area of section 87 is as great or greater than the comparable area of any other section along the length of the nozzle portion 65. And a visual comparison of FIGS. 13 and 14 demonstrates that the cross-sectional area of the first inlet section 83 is no less than (and is preferable about equal to) the cross-sectional area of the first nozzle section 87.

Figure 9:
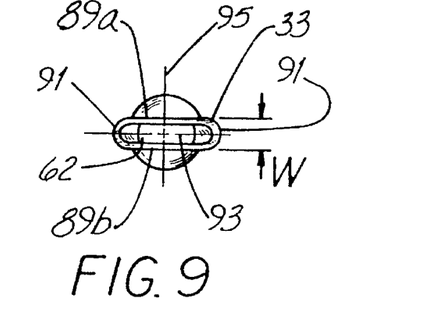
FIG. 9 is an end elevation view of the nozzle portion shown in FIG. 8 taken along the viewing plane 9—9 thereof.
Figure 10:
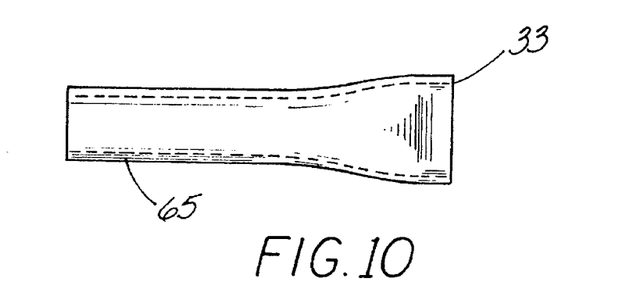
FIG. 10 is a top plan view of the nozzle portion shown in FIGS. 8 and 9 taken along the viewing plane 10—10 of FIG. 8.

In one highly preferred embodiment, the interior passage 79 of the air flow tube 25 is circular in cross-section along most of its length, i.e., up to that part of the nozzle portion 65 at which such portion 65 necks down and fans out to define the exit mouth 33. As best seen in FIG. 9, a preferred exit mouth 33 has an area 62 and first and second side edges 89a and 89b, respectively, which are generally parallel to one another. The mouth 33 has rounded end edges 91 and the resulting mouth shape resembles that of a race track.

Figure 15:
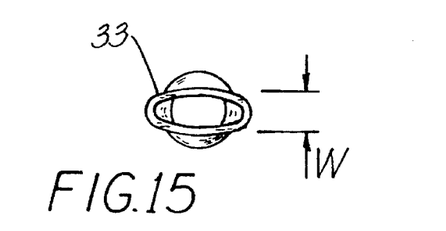
FIG. 15 is an alternate embodiment of the exit mouth of the sensor air flow tube.
Figure 16:
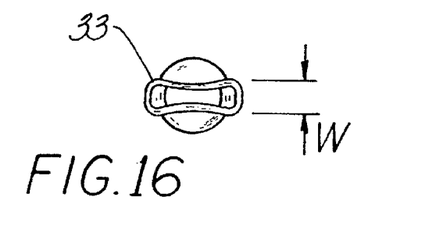
FIG. 16 is another alternate embodiment of the exit mouth of the sensor air flow tube.

While the exit mouth 33 shown in FIG. 9 is preferred, there are other possibilities. For example, FIG. 15 shows an ovoid mouth 33 and FIG. 16 shows a somewhat bow-shaped mouth 33. However, it is preferred that the maximum width "W" of any mouth 33 be about equal to or at least not appreciably greater than the diameter of the beam of light 21. Maintaining that width relationship helps assure that all or substantially all of the air-entrained particles 23 flowing out of the exit mouth 33 pass through the beam of light 21. On the other hand, an elongate exit mouth 33 helps assure reduced pressure drop as compared to, say, a circular exit mouth having a diameter about equal to the diameter of the light beam 21.

Figure 5:
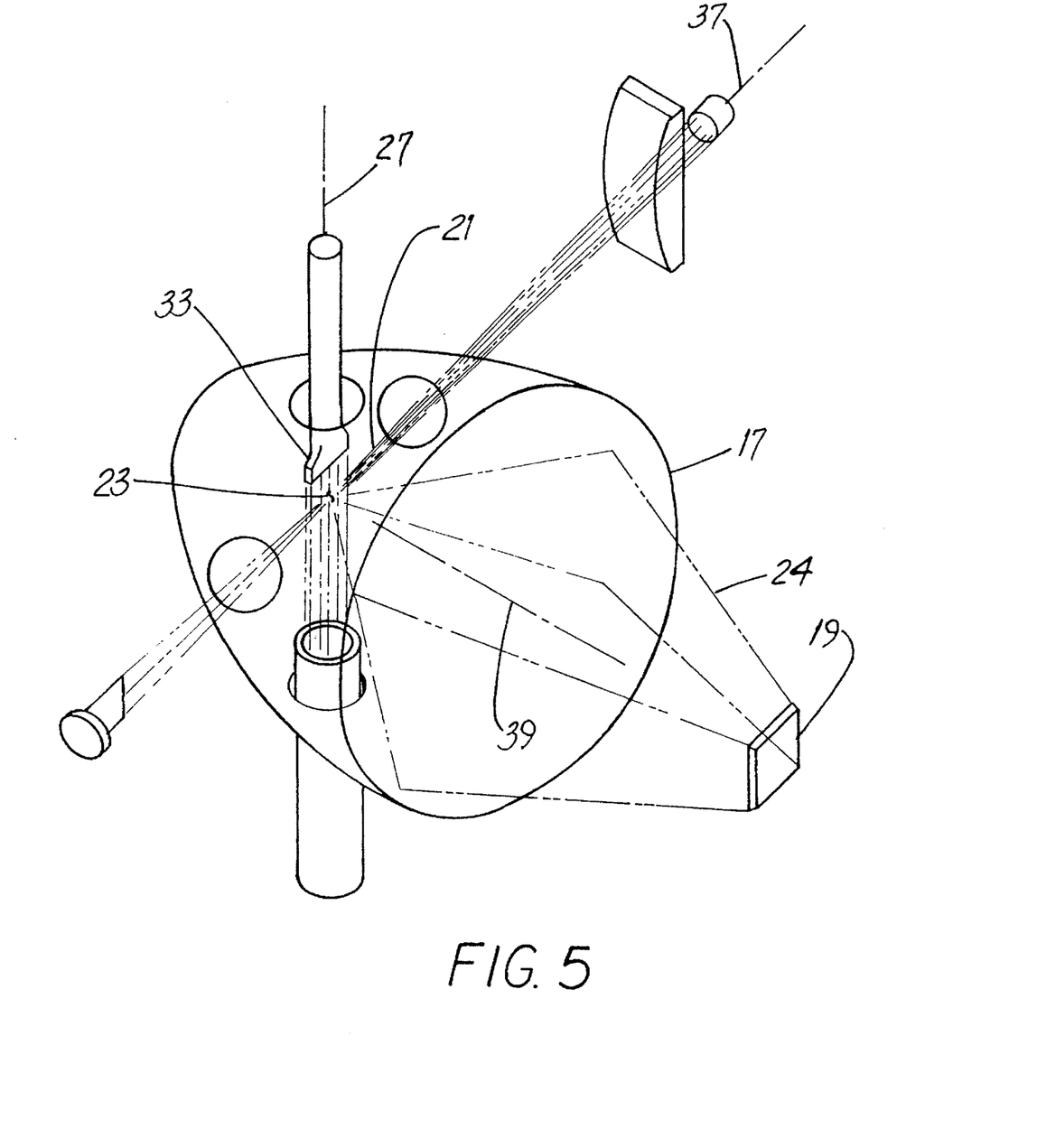
FIG. 5 is a spatial perspective view of aspects of the sensor shown in FIGS. 1–4.
Figure 6:
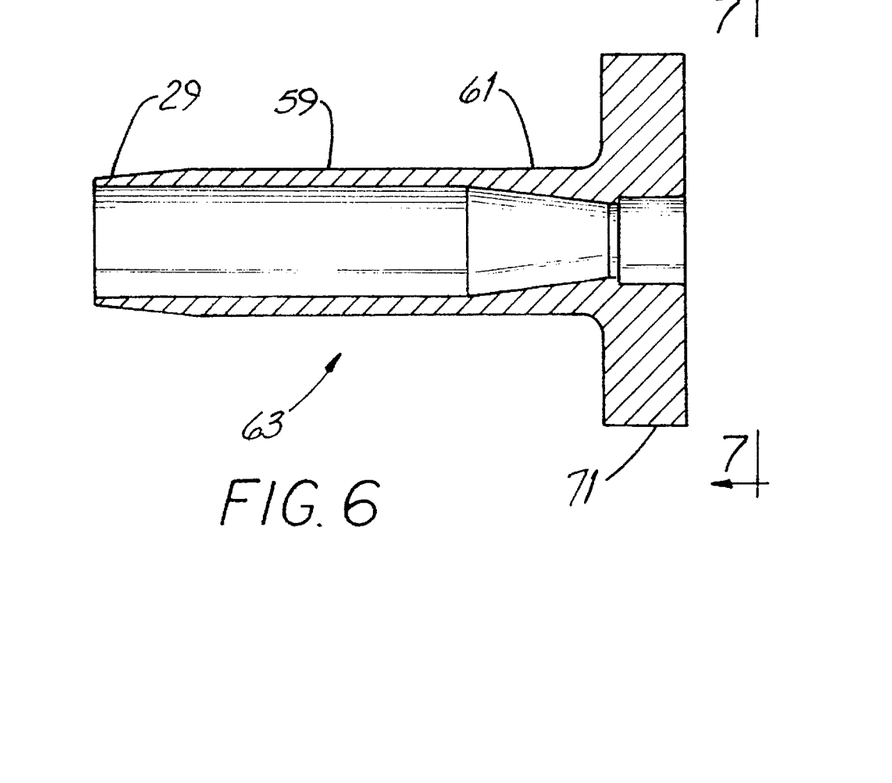
FIG. 6 is a side elevation view in cross-section of the inlet portion of the sensor air flow tube.
Figure 7:
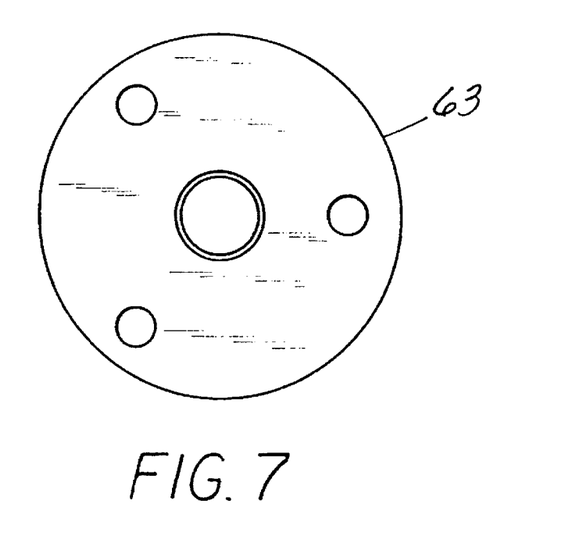
FIG. 7 is an end elevation view of the inlet portion shown in FIG. 6 taken along the viewing plane 7—7 thereof.
Figure 8:
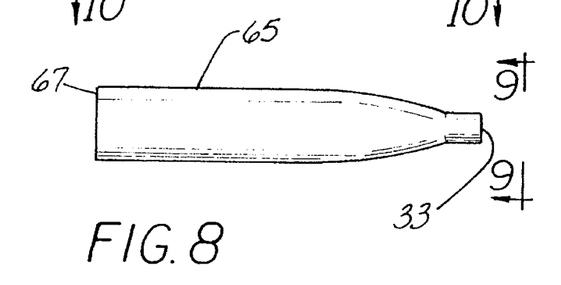
FIG. 8 is a side elevation view of the nozzle portion of the sensor air flow tube.

And there are also other relationships that characterize the preferred embodiment. Referring to FIGS. 5 and 9, the exit mouth 33 has a major axis 93 and a minor axis 95 generally normal to one another. The mouth 33 is oriented so that the major axis 93 is generally parallel to and spaced slightly from the beam long axis 37. Considered another way, the exit mouth 33 is elongate in a direction substantially parallel to the beam long axis 37.

Referring again to FIGS. 1, 2 and 3, the cavities 15 and 43 are separated by a wall 97 having a wall aperture 99. The blower 45 is mounted to an annular plate 101 which has an opening 102 through it and the blower 45 itself has a side air entry port 103 through which the blower 45 draws air for expulsion through the exhaust port 105. In a preferred arrangement, the wall aperture 99, the plate opening 102 and the air entry port 103 are in registry with the flow axis 27 and, most preferably, are generally concentric with such axis 27.

From the foregoing, it is to be appreciated that all of the air passing through the blower 45 is drawn from and first through the air flow tube 25. Blower-generated contaminants, e.g., paint chips, metal "fines" and the like, do not contaminate the air stream and do not enter the sensing cavity 15 where they might impair the accuracy of the sensor 10. To put it another way, the blower 45 is used "inside out" with respect to its conventional use mode.

The blower air entry port 103 on the intake side of the cage-like rotor is in flow communication with the exit mouth 33. The blower 45 thereby provides, in the form of a pressure differential between the inlet end 29 and the exit mouth 33 of the air flow tube 25, the "motive force" moving air through the tube 25.

Referring again to the FIGURES, in operation, the blower 45 is energized and air (usually with at least some particles 23 entrained therein) is drawn into the inlet end 29 of the air flow tube 25. The air-propelled particles 23 are expelled from the exit mouth 33 and "fly" through the laser light beam 21. Light 21 reflected by such particles 23 is received by the mirror 17 and reflected to a detector 19 for electronic analysis.

Air and entrained particles 23 continues to flow through the aperture 99, the opening 102 and the port 103 in the blower 45 and is discharged by the blower 45 through its exhaust port 105. Such air is urged through a coarse filter disc 107 which helps "smooth" air flow from turbulent to laminar flow. A major portion of the air is then simply exhausted through the openings and "free-flows" through the blower cavity 43 and exhaust filter 57 at the bottom of such cavity.

A relatively small percentage of the air from the blower exhaust port 105 enters a barbed fitting 109 and flows along the tubing 111 and through the flow sensor 53. From the sensor 53, such air flows along the tubing 113 and back into the blower cavity 43 from which it, too, free-flows out the exhaust filter 57.

It has been found that the new sensor 10 exhibits no greater pressure drop than 7–10 inches of water along the air flow tube and, more typically, such pressure drop is about 3 inches of water. This is a startling contrast to the pressure drop of 25–70 inches of water exhibited by prior art sensors.

While the principles of the invention have been described in connection with a few preferred embodiments, it is to be understood clearly that such embodiments are by way of example and are not limiting.

We claim:

1. A particle sensor using scattered light for analyzing airborne particles entrained in air drawn from an environment into the particle sensor, such sensor including:

a variable-speed centrifugal blower having a housing, a motor and an exhaust port;

an opening in the blower housing;

a particle detection system including a sensing portion having a light-scatter sensing cavity;

an air flow tube and a low-pressure-drop nozzle in air flow communication with the sensing cavity and with the opening in the blower housing;

a circuit connected to the motor for providing a speed-controlling variable voltage to the motor;

a flow sensor for providing a speed-affecting signal to the circuit;

an exhaust filter interposed between the exhaust port and the environment;

and wherein:

the particle detection system further includes (a) a light source, (b) a device directing light scattered by a particle entering the cavity through the air flow tube and the nozzle, and (c) a detector for receiving light directed by the device; and the air flowing in the sensing cavity through the air flow tube is drawn through such sensing cavity by the centrifugal blower, flows at a flow rate dependent upon the speed of the blower motor and is discharged from the particle sensor through the exhaust filter.

2. The particle sensor of claim 1 wherein:

the air flow tube extends along a linear flow axis;

the opening in the blower housing is an air inlet port; and the rate at which air flows along the air flow tube and into the opening in the blower housing is dependent upon the speed of the blower motor.

3. The particle sensor of claim 2 wherein:

the circuit is of the closed loop feedback type;

air flows along an air flow path which includes the air flow tube, the opening of the blower housing and the exhaust port; and a sensing device is in communication with the air flow path for providing a feedback signal to the circuit.

4. A particle sensor using scattered light for analyzing airborne particles entrained in air drawn from an environment into the particle sensor, such sensor including:

a light source illuminating a particle in the sensor;

a particle detection system having a sensing cavity with a detector for receiving light scattered by the particle;

a centrifugal blower powered by a variable-speed motor for flowing air through the sensing cavity;

a device connected to the motor for controlling the speed of the motor;

a single air flow tube in air flow communication with the environment, the sensing cavity and the blower;

and wherein:

the air flow tube has an inlet opening in flow communication with the environment and such opening is the sole inlet for air flowing through the particle sensor;

the air flowing through the sensing cavity flows at a flow rate dependent upon the speed of the blower motor;

the air flow tube, sensing cavity and centrifugal blower are in series;

air flowing through the air flow tube and the sensing cavity is moved solely by the centrifugal blower.

* * * * *

UNITED STATES PATENT AND TRADEMARK OFFICE
CERTIFICATE OF CORRECTION

PATENT NO. : 5,600,438
DATED : February 4, 1997
INVENTOR(S) : Gerhard Kreikebaum and David L. Chandler It is certified that error appears in the above-indentified patent and that said Letters Patent is hereby corrected as shown below:

In column 5, line 4, delete "axid" and insert --axis--.

In column 6, line 60, after "beam", insert --of light--.

In column 6, line 60, before "Light", insert --Beam of--.

Signed and Sealed this

Fifteenth Day of April, 1997

Attest:

BRUCE LEHMAN

Attesting Officer        Commissioner of Patents and Trademarks